(12) United States Patent
Nandi et al.

(10) Patent No.: US 9,708,243 B2
(45) Date of Patent: Jul. 18, 2017

(54) PROCESS FOR PREPARING 4-AMINODIPHENYLAMINE

(75) Inventors: Chinmoy Nandi, Mumbai (IN); Narendra Gangal, Mumbai (IN); Pramod Purohit, Mumbai (IN); Vinay Ketkar, Mumbai (IN); Dilip Kashelikar, Mumbai (IN)

(73) Assignee: NOCIL LIMITED, Mumbai (IN)

( * ) Notice: Subject to any disclaimer, the term of this patent is extended or adjusted under 35 U.S.C. 154(b) by 0 days.

(21) Appl. No.: 14/383,182

(22) PCT Filed: Mar. 7, 2012

(86) PCT No.: PCT/IB2012/051059
§ 371 (c)(1),
(2), (4) Date: Sep. 5, 2014

(87) PCT Pub. No.: WO2013/132290
PCT Pub. Date: Sep. 12, 2013

(65) Prior Publication Data
US 2015/0045584 A1 Feb. 12, 2015

(51) Int. Cl.
*C07C 209/68* (2006.01)
*C07C 209/02* (2006.01)
*C07C 209/36* (2006.01)

(52) U.S. Cl.
CPC .......... *C07C 209/68* (2013.01); *C07C 209/02* (2013.01); *C07C 209/36* (2013.01)

(58) Field of Classification Search
None
See application file for complete search history.

(56) References Cited

U.S. PATENT DOCUMENTS

| | | | |
|---|---|---|---|
| 4,122,118 A | 10/1978 | George et al. | |
| 4,140,716 A | 2/1979 | Maender et al. | |
| 4,155,936 A | 5/1979 | Sturm | |
| 4,187,248 A | 2/1980 | Merten et al. | |
| 4,187,249 A | 2/1980 | Maender et al. | |
| 4,196,146 A | 4/1980 | Merten et al. | |
| 4,209,463 A | 6/1980 | Maender et al. | |
| 4,479,008 A | 10/1984 | Batorewicz et al. | |
| 4,518,803 A | 5/1985 | Batorewicz et al. | |
| 4,614,817 A | 9/1986 | Maender et al. | |
| 4,670,595 A | 6/1987 | Podder et al. | |
| 4,683,332 A | 7/1987 | Sturm | |
| 5,117,063 A | 5/1992 | Stern et al. | |
| 5,453,541 A | 9/1995 | Stern et al. | |
| 5,608,111 A | 3/1997 | Stern et al. | |
| 5,623,088 A | 4/1997 | Stern et al. | |
| 5,739,403 A | 4/1998 | Reinartz et al. | |
| 5,977,411 A | 11/1999 | De Vera | |
| 6,140,538 A | 10/2000 | Rains et al. | |
| 6,365,933 B1 | 4/2002 | Yamazaki et al. | |
| 6,495,723 B1 | 12/2002 | De Vera et al. | |
| 6,583,320 B2 | 6/2003 | Triplett, II et al. | |
| 6,770,189 B2 | 8/2004 | Giatti et al. | |
| 7,084,302 B2 | 8/2006 | Feng et al. | |
| 7,176,333 B2 | 2/2007 | Wang et al. | |
| 7,183,439 B2 | 2/2007 | Triplett, II et al. | |
| 7,235,694 B2 | 6/2007 | Feng et al. | |
| 2002/0055652 A1 | 5/2002 | Schelhaas et al. | |
| 2009/0048465 A1 | 2/2009 | Feng et al. | |

OTHER PUBLICATIONS

Chandrakanthi, N. et al., "Preparation and characterization of fully oxidized form of polyaniline", *Polymer Bulletin*, 45: 113-120 (2000).
Stejskal, J. et al., "Accelerating effect of some cation radicals on the polymerization of aniline", *Polymer*, 36(21): 4135-4140 (1995).
Barton, D. et al., "The thermal decomposition of azobenzene", *Canadian Journal of Chemistry*, 61: 1712-1718 (1983).
Wei, Y. et al., "A Study in the Mechanism of Aniline Polymerization", *Journal of Polymer Science Part A: Polymer Chemistry*, 27(7): 2385-2396 (1989).
Budyka, M. et al., "Thermolysis of azobenzene", *Russian Chemical Bulletin*, 42(9): 1495-1497 (1993).
Katritzky, A. et al., "Rubber Chemicals Derived from Conjugate Addition. II. Synthesis of a Novel Class of Benzoquinone Diimines", *Rubber Chem. Technol.*, 74: 927 (2001).

*Primary Examiner* — Clinton Brooks
(74) *Attorney, Agent, or Firm* — Merchant & Gould P.C.

(57) ABSTRACT

A process for preparing 4-aminodiphenylamine (4-ADPA) comprising steps of coupling of aniline with nitrobenzene in presence of a suitable base, e.g. tetramethylammonium hydroxide (TMAH), hydrogenation of the coupling mass, phase separation, hydrogenation of azobenzene in the separated organic mass and fractional distillation for 4-ADPA recovery. An improvement in 4-ADPA recovery and a lowering of tar formation are obtained due to azobenzene reduction prior to 4-ADPA isolation. Also a gain in volume productivity of 4-ADPA is obtained by suitably altering the batch cycle time of the coupling reaction.

37 Claims, No Drawings

PROCESS FOR PREPARING 4-AMINODIPHENYLAMINE

This application is a National Stage Application of PCT/IB2012/051059, filed 7 Mar. 2012, which application is incorporated herein by reference. To the extent appropriate, a claim of priority is made to the above disclosed application.

FIELD OF THE INVENTION

The present invention relates to a process for the manufacture of 4-aminodiphenylamine (4-ADPA), wherein 4-ADPA recovery is improved by reduction of azobenzene in the reaction mass, prior to 4-ADPA isolation by fractional distillation thereby reducing the amount of distillation residue containing tars. The present invention also relates to reductive alkylation of 4-ADPA and the alkylated p-phenylenediamine products used as antioxidants and antiozonants in rubber that may be obtained from 4-ADPA by reductive alkylation with ketones. Also, the present invention can provide better volume productivity, namely, increased 4-ADPA yield per hour per liter of reactor space, thus enhancing the commercial advantage of the process.

RELATED ART

4-ADPA is widely used as an intermediate in the manufacture of various alkylated derivatives viz. N-(1,3-dimethylbutyl)-N'-phenyl para-phenylenediamine (6PPD), N-(1,3-dimethylpentyl)-N'-phenyl-parapheylenediamine (7PPD), N-(isopropyl)-N'-phenyl-paraphenylenediamine (IPPD), having utility as antioxidants and antiozonants, as stabilizers for monomers and polymers and in various other specialty applications. For example reductive alkylation of 4-ADPA with methyl isobutyl ketone (MIBK) provides 6PPD which is extensively used as an antiozonant for protection of various rubber products, especially in tyre manufacture.

Conventionally, 4-ADPA is manufactured by reaction of aniline or formanilide with 4-chloronitrobenzene in the presence of base ($K_2CO_3$) to give 4-nitrodiphenylamine (4-NDPA), followed by reduction (See e.g. U.S. Pat. Nos. 4,187,248; 4,683,332; 4,155,936; 4,670,595; 4,122,118; 4,614,817; 4,209,463; 4,196,146; 4,187,249; and 4,140,716). In an alternative method, 4-ADPA is manufactured by reduction of the product obtained by nitrosation of diphenylamine with $NaNO_2$ followed by Fischer-Hepp rearrangement giving 4-nitrosodiphenylamine (4-NODPA) (See e.g. U.S. Pat. Nos. 4,518,803 and 4,479,008)

A more economical and greener route has emerged involving the direct coupling of aniline and nitrobenzene in the presence of a base to give a mixture of 4-nitrosodiphenylamine (4-NODPA) and 4-nitrodiphenylamine (4-NDPA) along with some azobenzene and phenazine as by-products. This coupling reaction is followed by catalytic hydrogenation in presence of water to give 4-ADPA and regenerated base. The base is separated as part of an aqueous layer which is recycled to the process. 4-ADPA is obtained by fractional distillation of the organic phase, as disclosed in a series of patents (See e.g. U.S. Pat. Nos. 5,117,063; 5,453,541; 5,608,111; 5,623,088; 5,977,411; 6,140,538; 6,365,933; 6,583,320; 6,495,723; 6,770,189; 7,183,439; 7,084,302; 7,176,333; 7,235,694; and 5,739,403). Various other aspects of the process viz. reaction conditions, optimum molar ratios of reactants, types of catalyst used, recycle of raw materials, especially the base and aniline, recycle of catalyst etc. are also mentioned in these patents. This process can be run either in a batch or continuous manner.

The processes for the separation of 4-ADPA and reaction by-products such as azobenzene and phenazine are also described in these patents. Typically, 4-ADPA is separated by fractional distillation in distillation column at high temperature and under reduced pressure. The azobenzene by-product obtained by this fractional distillation, is catalytically hydrogenated to convert it to aniline that is recycled to the initial reaction. However, this fractional distillation process leads to loss of 4-ADPA by oxidative degradation and considerable tar formation. This causes not only a reduction in the yield of valuable 4-ADPA, but also creates a need to handle and dispose of the tar that is formed in the bottom product of the distillation column, by, for example, incinerations. Also some of the tarry substances are carried over with the distilled 4-ADPA and subsequently poison the catalyst used in the subsequent reductive alkylation step to manufacture alkylated paraphenylenediamines from 4-ADPA. These issues do not appear to be addressed by the prior art processes.

In the method of, for example, example 13 of U.S. Pat. No. 5,608,111 addition of nitrobenzene is carried out over a three hour period and during this addition, water and aniline are continuously removed from the reaction mixture by distillation under reduced pressure at 55 torr until about 100% conversion of nitrobenzene is achieved. This patent illustrates the continuous removal of water from the reaction of aniline, nitrobenzene and tetramethyl ammonium hydroxide (TMAH) by distillation under reduced pressure, indicating that the water is removed from the reactor as an aniline/water azeotrope.

OBJECTS OF THE INVENTION

The volume productivity of this reaction can be substantially improved by carrying out the process either in batch or continuous manner, wherein, nitrobenzene is added all at once thereby providing a substantial reduction in the total reaction time by avoidance of the three hour nitrobenzene addition period.

The downstream processes for separation of 4-ADPA and by-products generated by the reaction, e.g. azobenzene, phenazine and others, have also been described in the above-mentioned patents. For example, fractional distillation in a distillation column at high temperatures and under reduced pressure conditions has been employed for this purpose. The azobenzene obtained by fractional distillation, is then catalytically hydrogenated to aniline that may be recycled to the coupling reaction.

However it is observed that the downstream processes for separation of 4-ADPA and by-products of the coupling reaction, as described in the prior art, by fractional distillation in distillation column at high temperatures under reduced pressure conditions, leads to loss of some of the desired product, 4-ADPA, by oxidative degradation, leading to considerable tar formation. This results not only in the loss of valuable 4-ADPA, but also poses the additional problem of handling of tars formed in the distillation column bottoms and creating the need to incinerate the tars. Also some of the tarry substances are carried over in the distilled 4-ADPA and these tarry substances can act as a severe catalyst poison in a subsequent reductive alkylation step to manufacture alkylated paraphenylenediamines. These issues are not addressed in the above-mentioned prior art.

One objective of the present invention is to enhance the volume productivity of 4-ADPA in terms of grams or kilograms product per hour per liter of reactor volume.

Another objective of certain embodiments of the present invention is to manage the problems arising out of the formation of azobenzene in processes for the manufacture of 4-ADPA and its impact on downstream 4-ADPA recovery.

Another objective of the present invention is to reduce tar formation during 4-ADPA recovery, thereby improving the recovery of 4-ADPA and reducing waste that has to be disposed of.

A further objective of the present invention is to improve overall productivity and economics of the process.

SUMMARY OF THE INVENTION

In a first aspect, the present invention relates to a process for the preparation of 4-ADPA including the steps of:

i) reacting aniline and nitrobenzene in the presence of a base catalyst and water under conditions suitable to produce a reaction product including one or more salts of 4-NODPA and 4-NDPA along with one or more by-products including at least azobenzene;

ii) hydrogenating the reaction product from step i) in the presence of suitable hydrogenation catalyst and water to produce 4-ADPA-containing reaction product;

iii) separating the hydrogenation catalyst from the reaction mixture by filtration to obtain an aqueous phase containing at least base catalyst and an amount of organics, and an organic phase containing at least 4-ADPA, azobenzene and base catalyst; and iv) washing organic phase with water to reduce an amount of residual base catalyst in the organic phase and/or extracting the aqueous phase with an aromatic hydrocarbon solvent to reduce an amount of organics present in said aqueous phase In this aspect of the invention, increased recovery of base catalyst is obtained. In addition, undesirable by-products caused by the presence of residual base catalyst in the aniline recycle stream are reduced.

In a second aspect, the present invention relates to a process including steps (i)-(iv) above as well as the following additional steps:

v) dehydrating the organic phase containing at least 4-ADPA and azobenzene, in excess aniline to remove moisture under reduced pressure at temperature of about 100-110° C. to produce a dehydrated organic phase, vi) fractionally distilling the dehydrated organic phase below 130° C. under reduced pressure to obtain a concentrated organic mass having a desired aniline content;

vii) hydrogenating the concentrated organic mass from step (vi) in the presence of a suitable hydrogenation catalyst to reduce azobenzene into aniline;

viii) separating the hydrogenation catalyst from the product of step (vii) by, for example, filtration to produce a filtrate;

ix) fractionally distilling the separated product of step (viii) to recover 4-ADPA under reduced pressure; and x) optionally recycling the recovered aniline and hydrogenation catalyst to the process.

In this aspect of the invention, reduced tar formation is achieved due to azobenzene reduction prior to 4-ADPA isolation and 4-ADPA recovery is improved by reduction of azobenzene in the reaction mass prior to 4-ADPA isolation by fractional distillation which results in less formation of distillation residue containing tars.

In yet another aspect of the invention, a process is provided wherein at least some azobenzene, present in a reaction product obtained by hydrogenation of a coupling reaction product of aniline with nitrobenzene in the presence of a base catalyst, is hydrogenated to aniline, before isolation of 4-ADPA from the hydrogenated coupling reaction product.

In yet another aspect of the invention, a process is provided that comprises the steps of:

1) reacting aniline and nitrobenzene in the presence of a base catalyst and water under conditions suitable to produce a reaction product including one or more salts of 4-NODPA and 4-NDPA along with one or more by-products including at least azobenzene;

2) hydrogenating the reaction product from step 1) in the presence of suitable hydrogenation catalyst and water to produce 4-ADPA-containing reaction product;

3) separating the hydrogenation catalyst from the reaction mixture by filtration to obtain an aqueous phase containing at least base catalyst and an amount of organics, and an organic phase containing at least 4-ADPA, azobenzene and base catalyst;

4) washing the organic phase from step (3) with water to remove at least some residual base catalyst from the organic phase in an aqueous wash and mixing the aqueous wash with the aqueous phase to form an aqueous base catalyst recycle phase, 5) extracting the aqueous base catalyst recycle phase from step (4) with an aromatic hydrocarbon to remove at least some residual organic phase from the aqueous base catalyst recycle phase, and 6) recycling the extracted aqueous base catalyst recycle phase from step (5) containing the regenerated base to step (1), with optional further purification as per requirement.

Another embodiment of the present invention comprises the following steps in addition to the above:

7) dehydrating the organic phase in an excess of aniline to remove moisture under reduced pressure at a temperature of 100-110° C.;

8) fractionally distilling the dehydrated organic phase while maintaining a bottom temperature below 130° C. under reduced pressure for a sufficient time to obtain a product containing at least 4-ADPA and azobenzene and having an aniline content of less than 10% w/w;

9) hydrogenating the product of step 8) in the presence of suitable catalyst to reduce azobenzene to a content of less than 500 ppm, thereby increasing the aniline concentration;

10) separating the product of step 9) from the hydrogenation catalyst;

11) fractionally distilling the separated product from step 10) to recover 4-ADPA under reduced pressure and 12) optionally recycling catalyst from steps (3) and (10) to steps (2) and (9) respectively, optionally including the step of adding fresh catalyst to maintain a desired catalyst activity.

Other embodiments of the present invention encompass details of flow schemes and reaction mixtures all of which are hereinafter disclosed in the following discussion of each of the facets of the present invention.

DETAILED DESCRIPTION OF THE INVENTION

The present invention relates to a process for manufacturing 4-ADPA that is economically attractive. More particularly, in a first embodiment the invention provides a process in which the coupling reaction between aniline and nitrobenzene in the presence of base under suitable conditions (hereinafter "the coupling reaction") is carried out in a manner which completes the reaction faster than as per the teachings of the U.S. Pat. Nos. 5,608,111; 5,453,541; and 5,117,063, thereby increasing the volume productivity of the process, making the process economically more attractive.

As per example 13 of U.S. Pat. No. 5,608,111, during the coupling reaction, nitrobenzene is added to the mixture of aniline and TMAH base at a pressure of 55 torr over 3 hours with continuous removal of an aniline/water mixture. This leads to at least 98% conversion of nitrobenzene. The reported typical yields at 100% conversion of nitrobenzene are 4-nitrosodiphenylamine 92.1%, 4-nitrodiphenylamine 3.4%, azobenzene 3.4%, and phenazine 0.9%.

The process for manufacturing 4-ADPA of the present invention includes the steps of:

(i) reacting aniline and nitrobenzene in the presence of a suitable base under conditions sufficient to produce a reaction product including one or more of 4-nitrosodiphenylamine (4-NODPA), 4-nitrodiphenylamine (4-NDPA) and/or salts thereof (hereinafter also referred to as "4-ADPA intermediates") along with by-products including at least azobenzene;

(ii) hydrogenating the reaction product of step (i) in the presence of a suitable hydrogenation catalyst and water;

(iii) separating the hydrogenation catalyst from the reaction product of step (ii) by filtration or any other suitable means of separation to obtain a mixture of an aqueous phase and an organic phase, and separating the organic phase from aqueous phase.

In step (i) of the present invention, aniline is reacted with nitrobenzene in the presence of a suitable base such as tetramethylammonium hydroxide (TMAH) base under conditions suitable to produce a reaction mass containing Tetramethyl ammonium (TMA) salts of 4-nitrosodiphenylamine and/or 4-nitrodiphenylamine along with by-products including at least azobenzene and phenazine. The base catalyst employed in step (i) may be any suitable, conventional base catalyst known for use in the coupling reaction of aniline with nitrobenzene. Exemplary base catalysts include tetraalkylammonium hydroxides such as tetramethylammonium hydroxide (TMAH), tetrapropylammonium hydroxide, benzyl-trimethylammonium hydroxide, tetrabutylammonium hydroxide, phenytrimethylammonium hydroxide, carbonate salts of any of the foregoing and mixtures thereof.

The molar ratio of water to the base charged to the reaction mixture for this step (i) may be up to about 10:1, more preferably up to 9.5:1 at the start of the reaction of aniline with nitrobenzene.

The molar ratio of aniline to nitrobenzene charged to the reaction mixtures of step (i) is from about 6:1 to about 15:1, more preferably, from about 6:1 to about 10:1. The molar ratio of base to nitrobenzene charged to the reaction mixture of step (i) is from about 0.8:1 to about 1.5:1, and, more preferably, from about 0.9:1 to about 1:1.

The total reaction time for reaction of aniline with nitrobenzene in the coupling reaction of step (i) may be less than 3.5 hours and, may be less than 1.5 hours. The coupling reaction may otherwise be carried out under conventional conditions of temperature and pressure.

To improve the volume productivity of this coupling reaction, in one aspect the present invention adds the nitrobenzene in less than 3 hours, typically in one lot, and employs a reaction time of about 1 hour, thereby reducing the batch cycle time of the reaction (empty-to-empty) to nearly half the batch cycle time exemplified in Example 13 of U.S. Pat. No. 5,608,111. This leads to about a two-fold increase in the volume productivity of the coupling reaction.

The faster addition of nitrobenzene to the coupling reaction, however, leads to an increase in the azobenzene content of the products of the coupling reaction and hence a lower selectivity for the desired 4-ADPA product. However, this decreased selectivity for 4-ADPA is more than offset by the improved volume productivity of the process when evaluated in terms of gm/hr/liter or kg/hr/m³ of each batch. Further, since azobenzene is reduced to the starting material aniline in a subsequent hydrogenation step, the reduced azobenzene can then be recycled to the coupling reaction in the form of aniline.

In step (ii), hydrogenation is performed in the presence of about 20 to about 50 wt % of water, relative to total mass for hydrogenation at the start of hydrogenation. Step (iii) where hydrogenation catalyst is separated from the hydrogenated reaction mixture is carried out at a temperature of from about 20 to about 60° C.

In an exemplary embodiment, the process for manufacturing 4-ADPA may involve the following additional steps:

(iv) washing the organic phase from step (iii) with water to remove at least some residual base catalyst from the organic phase in an aqueous wash and mixing the aqueous wash with the aqueous phase to form an aqueous base catalyst recycle phase, (v) extracting of the aqueous base catalyst recycle phase from step (iv) with an aromatic hydrocarbon to remove at least some residual organic phase from the aqueous TMAH recycle phase, and (vi) recycling the extracted aqueous base catalyst recycle phase from step (v) containing the regenerated base to step (i), with optional further purification as per requirement.

In step (iv), a weight ratio of water to organic phase is from 0.1:1 to 1:1, and more preferably, from 0.2:1 to 0.6:1. In step (iv), a weight ratio of aromatic hydrocarbon solvent to aqueous phase is from 0.1:1 to 1:1, more preferably, from 0.1:1 to 0.4:1. In step (iv), the aromatic hydrocarbon solvent preferably comprises benzene, toluene, xylene and mixtures thereof. Step (iv) may be carried out at a temperature of 20-40° C. The aqueous phase from step (iv) containing base catalyst may be used to form a subsequent reaction mixture for use in step (i).

In the extraction step (v), the aromatic hydrocarbon solvent may be selected from benzene, toluene, xylene, and the like, as well as mixtures thereof. The weight ratio of the aromatic hydrocarbon solvent to the aqueous phase in extraction step (v) is from about 0.1:1 to about 1:1, more preferably from about 0.1:1 to about 0.4:1.

It has been found that during the conventional processes for the recovery/isolation of aniline, azobenzene, phenazine and 4-ADPA by fractional distillation of the organic phase resulting from the production of 4-ADPA, under reduced pressure and at high temperature, there is substantial degradation or reaction of azobenzene and 4-ADPA. Also, it has been found that more aniline is recovered during distillation than can be accounted for by analysis of the feed to the distillation step, thereby indicating that additional aniline is formed by reaction during distillation. Upon detailed investigation, it was found that the molar loss of azobenzene is nearly proportional to the molar gain in aniline during distillation. This indicates that azobenzene undergoes thermal decomposition under the conditions used for distillation to aniline and/or that azobenzene is reduced to aniline during distillation.

Thermal decomposition of azobenzene to aniline is reported in the literature at high temperature. See e.g. M. F.

Budyka et. al., Russian Chemical Bulletin, vol. 42 (9), pp. 1495-1497, (1993) and Donald Barton et al, Canadian Journal of Chemistry, vol. 61, pp 1712-1718 (1983)). It is also known in the literature that 4-ADPA is susceptible to oxidation to produce quinone-diimines similar to hydroquinone-quinone system. 4-ADPA is also known to be susceptible to oxidative polymerization to polyanilines such as emeraldine base and its various isomers. (See e.g. Alan R Katritzky et al., Rubber Chem. Technol., 74, 927 (2001); Yen Wei et al., Journal of Polymer Science Part A: Polymer Chemistry, Vol. 27, Issue 7, pp. 2385-2396 (1989); Jaroslav Stejskal et al., Polymer, Vol. 36, Issue 21, pp. 4135-4140 (1995) and Nayana Chandrakanthi et al., Polymer Bulletin, 45, pp. 113-120 (2000)).

It is also observed from the material balance of organic mass that besides loss of azobenzene, considerable 4-ADPA is lost in the distillation step, generating, for example, tarry by-products. Thus it can be envisaged that under high temperature conditions during distillation, a redox system is generated wherein azobenzene is reduced to aniline while 4-ADPA is oxidized to higher molecular weight compounds, resulting in tar formation.

A simulated study was conducted by heating a mixture of pure azobenzene and 4-ADPA in a similar weight ratio as is present in the organic stream of the 4-ADPA production process at varying temperatures of 220-250° C. (similar to the 4-ADPA distillation temperatures) under atmospheric pressure using a nitrogen blanket. This study reveals that aniline is formed in an amount almost equivalent to the amount of azobenzene that is reduced. The study also confirmed that the rate of aniline formation was faster at higher temperatures and accompanied by a equivalent loss of 4-ADPA. This demonstrates that fractional distillation to separate azobenzene at higher temperature in the presence of 4-ADPA is not desirable as some 4-ADPA is converted to tar, in a correspondingly lower recovery of 4-ADPA, difficulties in operation of the distillation step due to the problems encountered in the removal of the tar-containing distillation bottoms product and its disposal.

For example, tar formation leads to recovery of less azobenzene, difficulty in the distillation caused by the need to remove tar in the bottoms product of distillation and requires the additional undesirable step of tar disposal. Also, due to tar formation during the distillation process, the boiling point of the reaction mass increases thereby further reducing the recovery of 4-ADPA. Further, a high reflux is necessary to ensure the purity of 4-ADPA. Carryover of this tarry material with the 4-ADPA affects the subsequent reductive alkylation step used in the production of alkylated parapheneylenediamines such as 6PPD. Specifically, this tarry material adversely affects noble metal catalyst activity in the alkylation reaction, whereby the batch cycle time increases resulting in a decrease in the productivity of the reductive alkylation step per unit time. The tarry material also adversely affects catalyst consumption by poisoning the catalyst therefore reducing the cost effectiveness of the process.

The present invention solves these problems by removal of azobenzene from the 4-ADPA-containing reaction product before subjecting it to fractional distillation for 4-ADPA recovery. The approximately 2-fold increase in volume productivity, achievable via the first embodiment of the present invention, can be realized most effectively by also adopting a strategy of 4-ADPA isolation, which involves reduction of azobenzene prior to separation of 4-ADPA from the coupling reaction products by fractional distillation.

In another exemplary embodiment, the invention provides a process in which lower amounts of tarry by-products are formed during the steps of refining 4-ADPA product of the coupling reaction. More particularly, the invention provides a process in which less 4-ADPA is degraded during the steps used to purify the 4-ADPA from by-products of the coupling reaction, even when subjected to relatively drastic temperature conditions during distillation. This leads to improvement in the degree of 4-ADPA recovery and/or the 4-ADPA purity. Thus, this exemplary embodiment includes, in addition to steps (i)-(vi) above, one or more of the following steps:

(vii) dehydrating the organic phase containing at least 4-ADPA, azobenzene and phenazine in excess aniline to remove at least some moisture under reduced pressure at a temperature of about 100-110° C.;

(viii) fractionally distilling the dehydrated organic phase containing at least 4-ADPA, azobenzene and phenazine from step (vii) at a temperature below 130° C. under reduced pressure to obtain a concentrated organic mass with an aniline content less than 5% w/w;

(ix) hydrogenating the concentrated mass from step (viii) in the presence of a suitable hydrogenation catalyst to reduce at least some azobenzene to aniline and provide a reduced mass;

(x) separating the hydrogenation catalyst from the reduced mass of step (ix) by filtration or any other suitable means of separation to provide a filtrate;

(xi) fractionally distilling the filtrate to separate low boiling point materials under reduced pressure including at least aniline and phenazine to provide a distillate and bottoms;

(xii) recovering 4-ADPA having >99% purity from the bottoms;

(xiii) recycling aniline recovered from steps (viii) and (xi) to step (i); and (xiv) recycling hydrogenation catalyst from steps (iii) and (x) to steps (ii) and (ix) respectively, optionally including the step of adding fresh catalyst to maintain a desired catalyst activity.

In the dehydration step (vii) of the organic phase, containing 4-ADPA and at least azobenzene and phenazine in excess aniline, moisture is removed under a reduced pressure at about 100-110° C. Preferably, the organic phase is first washed with water to remove base catalyst for subsequent recycle, since the base catalyst used in the reaction is typically a significant element in the cost of 4-ADPA production.

The hydrogenated product may then be concentrated by distilling off aniline to a desired level, preferably from 0% w/w to less than 10% w/w, more preferably, from 2% w/w to less than 7% w/w, and most preferably to a level of about 5% w/w, without subjecting the reaction mass to a high temperature. Preferably the distillation temperature is not above about 130° C. It has been found that up to about 130° C., azobenzene is fairly stable in the organic mass. Thus, preferably aniline is removed to the maximum possible extent under reduced pressure to concentrate the organic mass. It has been found that aniline concentration below 5% w/w can be achieved by controlling the organic mass temperature at less than 130° C. under a reduced pressure of 10 mm Hg.

The resultant mass is then hydrogenated in the presence of suitable catalyst at a temperature of from 70-140° C., more preferably 120-160° C. and at a suitable hydrogen pressure of, for example, from 1 to 35 kg/cm$^2$ to reduce azobenzene to aniline. Typically, the hydrogenation time is less than 2 hours. The reduced product is then subjected to fractional distillation to separate aniline and any remaining phenazine to thereby recover 4-ADPA with less tar formation. The method of the present invention, which employs reduction of the azobenzene in the organic phase before fractional distillation to separate 4-ADPA, provides an improvement in the method for recovery of aniline and 4-ADPA resulting in less tar formation during distillation, even under high temperature conditions.

In the fractional distillation step (viii), the temperature of the organic phase is maintained during distillation at about 70° C. to about 130° C. and the distillation is carried out at a reduced pressure of about 10 mm Hg to about 100 mm Hg. Preferably, during the fractional distillation step (viii), the organic phase is maintained at a temperature of about 100° to about 130° C. and the distillation is carried out at a reduced pressure of about 10 mm Hg to about 40 mm Hg. At the end of the fractional distillation of step (viii), the aniline content of the concentrated mass may be not more than about 10 wt %, and, more preferably, not more than about 6 wt. %. Higher aniline content (>10%) in step (viii) generate considerable impurities in subsequent hydrogenation step (ix), causing difficulty in later fractional distillation steps.

Typical hydrogenation catalysts for azobenzene reduction in step (ix) are supported noble metal catalysts, such as rhodium on carbon, ruthenium on carbon, platinum on carbon, palladium on carbon, and mixtures thereof, or other hydrogenation catalysts, such as Raney nickel, Raney copper, etc. Typically, hydrogen pressures of about 1 to about 35 Kg/Cm$^2$, preferably in the range of about 3 to about 25 Kg/cm$^2$, can be used for azobenzene reduction. The hydrogenation of step (ix) may be carried out at a temperature from about 70° C. to about 140° C., a pressure of about 1 kg/cm$^2$ to about 35 kg/cm$^2$ and for a hydrogenation time of less than about 2 hours, whereby at least some azobenzene is reduced to aniline.

In step (xi), the fractional distillation may be carried out at a bottoms temperature from about 245° C. to about 255° C. and a reduced pressure of about 6 mm Hg to about 12 mm Hg. The recovery of 4-ADPA in step (xii) may be carried out at a top temperature of from about 190° C. to about 200° C. and a pressure of from about 3 mm Hg to about 7 mm Hg.

In another embodiment, the present invention provides improved recovery of 4-ADPA and recycled base by a process for efficiently separating and purifying the separated organic and aqueous phases obtained after hydrogenation of the reaction product of the coupling reaction.

The organic and aqueous phases obtained after catalyst filtration need to be efficiently separated in order to improve the economics of the process by allowing more efficient recycle of the base catalyst and improved recovery of the desired 4-ADPA product. However, in large-scale operations employing various liquid-liquid separation methods, a prolonged period of time is required to accomplish the desired level of phase separation. Also, due to the partial solubility of aniline in the aqueous phase, some amount of aniline and product remains with the aqueous phase after separation of the organic phase therefrom. This may pose problems for efficiently and/or effectively recycling the base catalyst found in the aqueous phase back to the coupling reaction.

Thus, in order to maximize aniline and product recovery from the aqueous layer containing the base, a water immiscible solvent such as aromatic hydrocarbons like toluene, xylene, ethyl benzene etc. can be used to extract traces of aniline, 4-ADPA and other organics to further purify the aqueous phase containing the base catalyst. Thus a liquid-liquid extraction of aqueous base catalyst with such a water immiscible aromatic hydrocarbon solvent provides an improved method for purifying the base catalyst for effective recycle, while at the same time recovering additional valuable extractable organics such as 4-ADPA from aqueous phase.

Liquid-liquid extraction of the aqueous phase containing the base catalyst with a suitable aromatic hydrocarbon solvent can, for example, be carried out either as a multi-stage batch process or as a continuous counter-current process. The extraction is preferably carried out with a weight/weight (w/w) ratio of aqueous phase to solvent phase of 1:0.1 to 1:1, or more preferably, a ratio of 1:0.2 to 1:0.4. The extraction may be carried out at a temperature between 20-80° C., more preferably between 30-50° C., under atmospheric pressure.

The extraction serves to further purify the aqueous recycle stream containing the base catalyst by extracting the organics. For example, a liquid-liquid extraction of aqueous phase containing the base catalyst with toluene in a three stage batch manner with a phase ratio of 1:0.3 (w/w) aqueous phase to solve, or via continuous counter-current extraction with toluene in a suitable device (Mixer-Settler system, liquid-liquid extractor or packed bed column) provided an aqueous phase containing less than 100 ppm of residual organic material, mainly aniline. Virtually no organic impurity other than aniline was found in the purified aqueous phase containing the base catalyst.

Aqueous phase purified in this manner, followed by concentration to the desired level, provided consistency in the coupling reaction of aniline and nitrobenzene by favorably altering the composition of the base catalyst recycle stream as discussed above, thereby leading to a more economical production of 4-ADPA. The temperature of the hydrogenated coupling reaction product is maintained at 70° C. to 130° C., more preferably, 100° C. to 130° C. during the concentrating step and the concentrating step is carried out at reduced pressure of 10 to 100 mm Hg, more preferably, 10 to 40 mm Hg.

The concentrating step is carried out until an aniline content of not more than 10 wt %, preferably not more than 6 wt %, is achieved.

The organic layer obtained in the initial separation of step (iii) above also contains some traces of base catalyst, e.g. TMAH, which can cause formation of impurities in downstream distillation steps, This is because base catalyst may decompose in the presence of excess aniline at high temperature to give rise to N-methyl aniline. N-methyl aniline has a boiling point and relative volatility very close to that of aniline and hence is accumulated over a period time in the aniline recycle. Also N-methyl aniline also may undergo a coupling reaction with nitrobenzene under the reaction conditions used to couple aniline and nitrobenzene, thereby resulting in N-methyl derivatives of 4-NODPA and 4-NDPA. Thus it is important in commercial production of 4-ADPA, to remove traces of the base catalyst found in this organic layer in order to improve the consistency in the composition of the recycle of recovered aniline. Otherwise, the N-methyl derivatives of 4-NODPA and 4-NDPA may increase over a period of time due to decomposition of residual TMAH remaining in the organic streams obtained from various distillation steps.

It was found that organic phase after separation in step (iii) contains approximately 2000-4000 ppm of base catalyst, e.g. TMAH. Thus, to recover some of this base catalyst from the organic layer, the organic layer is extracted with de-mineralized water in a (w/w) ratio of organic phase:water of 1:0.1 to 1:0.6, or more preferably in a w/w ratio of organic phase:water of 1:0.3 to 1.0:0.4. This extraction may also be carried out as a multi-stage batch process or as a continuous counter-current process in a suitable device (Mixer-settler system, liquid-liquid extractor with rotating shaft or in packed column) at 20-80° C., preferably at 40-60° C. The extraction is typically carried out under atmospheric pressure.

For example, an organic stream containing 4000 ppm of TMAH, extracted in a continuous counter-current process with water at an organic phase:water ratio of 1:0.4 at 50° C. provided an organic phase containing less than 20 ppm of TMAH. Thus the organic phase, purified in this manner, when subjected to a subsequent distillation step under reduced pressure for recovery of aniline and 4-ADPA, generated a negligible amount of N-methyl aniline in the aniline recycle stream. This shows that the purification of the organic phase by water extraction improves the consistency of the 4-ADPA production process and reduces formation of N-methyl aniline based impurities in the coupling reaction. This not only reduces loss of the valuable base catalyst, but also reduces aniline loss by reducing its conversion to N-methyl aniline and purging of the impurity enriched aniline fraction from the system. This will lead to better process economics due to a substantial reduction in impurity formation.

The 4-ADPA products obtained by any of the methods of the present invention may be further reacted by reductive alkylation of the 4-ADPA with suitable ketone to produce at least one alkylated derivative of 4-ADPA such as 6PPD and 7PPD.

The invention is further illustrated by the following examples, which are not intended to limit the scope of the invention in any way.

Analytical Methods:

HPLC Assay: Reverse phase HPLC was used to analyze the reaction mixtures. A 5 micron Lichrosphere RP-18e 250×4 6 mm internal diameter column was employed using Agilent 1200 with DAD coupled with Chemstation Software using an internal standard method.

Mobile phase gradient program shown in Table 1 below:
Mobile phase A: methanol HPLC grade
Mobile phase B: to 75% water and 25% methanol add 0.2-0.3 ml of triethyl amine and adjust the pH to 6.5 to 7.0 using $H_3PO_4$.

TABLE 1

| Time | A % | B % | Flow rate |
|---|---|---|---|
| 0.0 | 50 | 50 | 1.0 |
| 5.0 | 50 | 50 | 1.0 |
| 15 | 100 | 0 | 1.0 |
| 17 | 100 | 0 | 1.0 |
| 17.5 | 50 | 50 | 1.0 |
| 20 | 50 | 50 | 1.0 |

GC Method: A Shimadzu 2010 Gas Chromatograph coupled with GC Solution Software was employed using HP-5, the column was 10 meters in length with a 0.53 mm internal diameter, and a 2.65 μm film thickness was used.
Carrier: Nitrogen, 13.5 ml/min. flow.
FID Gases: $H_2$ at 30 ml/min. and air at 300 ml/min.
Detector-FID at 280° C.
Injection Port at 280° C.
Oven Programme 50(2)–15° C./min–280° C. (5 min.)

EXAMPLES

Example A—Conventional Coupling Reaction of Aniline with Nitrobenzene

This example illustrates the results obtained when laboratory experiments were conducted similar to Example 13 of U.S. Pat. No. 5,608,111.

The coupling reaction was carried out in a 2 liter Glass Round Bottom flask (RB flask) equipped with a stirrer (½ moon blade Teflon™ stirrer), Dean-Stark condenser, thermometer, Teflon™ baffle, dropping funnel for nitrobenzene addition. Initially 25% aqueous TMAH solution (24.8% w/w, 680.7 gm, 168.8 gm on 100% basis, 1.86 moles) was charged into the RB flask. Water was removed by distillation under reduced pressure at 55 mm Hg to obtain an aqueous TMAH solution of 35% w/w TMAH. During this stage the temperature increased to 50-53° C. Aniline was charged (1003.9 gm, 10.76 moles) into the reactor and the distillation was continued under reduced pressure at 55 mm Hg. Water and aniline were removed by azeotropic distillation until the molar ratio of water to TMAH was about 4:1. During this process the temperature of the reaction mass increased to 70-73° C.

After attaining the required mole ratio of water to base, nitrobenzene (218.3 gm, 1.77 moles) was added continuously over a period of 180 min During the nitrobenzene addition water and aniline were continuously being removed from the reaction by distillation under reduced pressure at 55 mm Hg. The reaction mass was maintained at about 75° C./55 mm Hg for 0.5 hr, after completion of nitrobenzene addition. The reaction end point was determined by HPLC analysis by monitoring the conversion of nitrobenzene. Total reaction time is about 5.5 hr. Typical selectivity determined by HPLC at the end of the hold period was a nitrobenzene conversion of 99.91%, 4-NODPA—85.4%, 4-NDPA—6.1%, azobenzene—7.3% and phenazine—1.2%. Moisture content at the end of batch was found to be 3.55% by GC (and by Material balance 3.23%) and water to base mole ratio was found to be about 1.32 (by material balance 1.20).

The volume productivity based on 4-ADPA (4-NODPA+ 4-NDPA) was calculated to be 29.34 gm/hr/liter.

The same reaction can be carried out using 35% TMAH (separately concentrated) instead of 25% TMAH, thereby decreasing the total reaction time to 4.5 hr. by omitting the step of distilling the 25% TMAH to concentrate it to 35% TMAH. The volume productivity of this variation, based on 4-ADPA (4-NODPA+4-NDPA) was 35.86 gm/hr/liter.

Example 1—Addition of Nitrobenzene in a Single Lot

This example illustrates the effect of addition of nitrobenzene in single lot after attaining the desired water to base mole ratio for the start of the coupling reaction, and its impact on volume productivity.

The reaction set up was the same as was used for Example A. Initially, aqueous TMAH solution (35% w/w, 480.5 gm, 168.18 gm on a 100% basis, 1.85 moles) was charged. Aniline was charged (1004.2 gm, 10.8 moles) into the reactor and distillation under reduced pressure was continued at 55 mm Hg. Water and aniline were removed by distillation until the molar ratio of water to TMAH was about 4:1. During this process the temperature of the reaction mass increased to 75° C. After attaining required mole ratio of water to base, nitrobenzene (218.7 gm, 1.78 moles) was added in single lot by using a dropping funnel. After nitrobenzene addition, water and aniline were continuously removed from the reaction by distillation under reduced pressure at 55 mm Hg. Samples of the reaction mass were drawn at ½ hr intervals for analysis by HPLC. The reaction was completed within 1 hour. The reaction end point was determined by HPLC analysis by monitoring the conversion of nitrobenzene. The total reaction time was about 2.1 hrs.

Typical selectivity determined by HPLC at 97% nitrobenzene conversion (about 3% NB in distillate) was: 4-NODPA 66.5%, 4-NDPA 13%, azobenzene 19.6% and phenazine 0.9%.

The volume productivity of the reaction based on 4-ADPA (4-NODPA+4-NDPA) was calculated to be 68.92 gm/hr/liter. This result shows that when nitrobenzene is added in one lot, the volume productivity yield of 4-NODPA and 4-NDPA, taken together, increases almost two fold as compared to the volume productivity of Example A.

Example B—Reduction of the Coupling Reaction Product

This example illustrates a typical example of reduction of 4-NODPA and 4-NDPA in coupling mass.

In 2 liter capacity autoclave, a coupling reaction product (900 gm) containing aniline (54%), TMA salt of 4-NODPA (25%), 4-NDPA (1.8%), phenazine (0.3%), azobenzene (1.8%) was placed. To this product was added water (307 gm) and noble metal catalyst (e.g. 5% Pd/C, 4 weight % loading on 4-NODPA+4-NDPA). The reaction mixture was heated at 80° C. under a hydrogen pressure of 15 kg/cm². At the end of reduction (no hydrogen absorption, typically 30 minutes), the unconverted 4-NODPA and 4-NDPA content was almost negligible (<100 ppm.).

Example 2—Purification of the Aqueous Phase Containing Base Catalyst

This example illustrates the purification of the separated aqueous phase of step (iv) of the method by extraction with an aromatic hydrocarbon solvent in accordance with the present invention.

Aqueous phase separated from the reduction mass of Example B as in step (iv) described above and containing aniline, 4-ADPA, azobenzene, phenazine, etc was purified by extracting with toluene three times at about 35° C. The phase ratio of aqueous phase to toluene was maintained at 1:0.25 w/w. The typical organic content of the aqueous phase prior to extraction with toluene was about 2% aniline, about 80 ppm azobenzene, about 100 ppm phenazine, about 1000 ppm 4-ADPA. The typical organic content of the aqueous phase after toluene extraction was about 100 ppm containing mostly aniline. This demonstrates that the extraction method of the present invention can be used to significantly reduce the quantity of undesirable materials present in the aqueous phase obtained by separation from the organic phase in step (iv) of the method.

Example 3—Purification of the Organic Phase to Reduce Base Catalyst Content

This example illustrates the purification of the separated organic phase from step (iv) of the method by extracting with demineralised water in accordance with the present invention.

Organic phase separated from reduction mass as in step (iv) described above and containing about 2000 ppm of TMAH is purified by extraction with fresh demineralised water three times at about 35° C. The phase ratio of organic phase to water was 1:0.2 w/w. The typical TMAH content of organic feed prior to extraction was about 2000 ppm which after the extraction process was reduced to about 10 ppm TMAH in the organic phase. This demonstrates that the extraction method of the present invention can be used to significantly reduce the quantity of base catalyst present in the organic phase obtained by separation from the organic phase in step (iv) of the method.

Example C—Fractional Distillation in the Presence of Azobenzene

This example illustrates the considerable tar formation and loss of azobenzene with a corresponding gain in aniline and the reduction in 4-ADPA content that occurs during fractional distillation at high temperature to recover 4-ADPA.

A 4-ADPA reaction mass (2000 gm) containing aniline (70%), azobenzene (2.2%), phenazine (0.2%), 4-ADPA (24.6%), moisture (2.9%), etc., when subjected to fractional distillation under a reduced pressure of up to 8-10 mm Hg and at a pot temperature of up to 270° C., generated an excess of aniline of about 1.2% relative to a calculated expected amount of aniline, based on the input stream, with a corresponding loss of azobenzene (32.5% based on input) and 4-ADPA (6.7%, based on input) respectively. A large amount of distillation residue containing tars and some 4-ADPA was also obtained.

Example D—Simulated Study of Stability of an Azobenzene and 4-ADPA Mixture

This example illustrates the effect of azobenzene on the stability of 4-ADPA at high temperature.

Distilled 4-ADPA (>99% pure) and re-crystallized azobenzene were mixed in a 4-necked glass round bottom flask equipped with an agitator, thermometer and a reflux condenser. The mixture was maintained at 220±2° C. with continuous agitation under nitrogen atmosphere. Samples were withdrawn at certain intervals and analyzed by gas chromatography. The results are shown in Table 2 below:

TABLE 2

| Distillation Time (hrs) | (%) Aniline | (%) Azobenzene | (%) 4-ADPA | (%) other materials |
|---|---|---|---|---|
| 0 | 0.04 | 5.9 | 95.7 | 0 |
| 2 | 0.7 | 4.1 | 95.2 | 0 |
| 4 | 0.93 | 2.23 | 92.50 | 4.34 |

A similar experiment to that described above was carried out at 250±2° C. and the results are shown in Table 3 below.

TABLE 3

| Sample (hrs) | (%) Aniline | (%) Azobenzene | (%) 4-ADPA | (%) other materials |
|---|---|---|---|---|
| 0 | 0.3 | 7.8 | 91.9 | 0 |
| 2 | 5.87 | 0.24 | 91.48 | 2.41 |
| 4 | 5.47 | 0.24 | 91.24 | 3.05 |
| 6 | 6.94 | 0.30 | 87.45 | 5.31 |

A similar experiment to that described above was carried out using the 4-ADPA reaction product of Example A and was distilled at 130±2° C. The results are shown in Table 4 below.

TABLE 4

| Sample (hrs) | (%) Aniline | (%) Azobenzene | (%) Phenazine | (%) 4-ADPA | (%) other materials |
|---|---|---|---|---|---|
| 0 | 3.6 | 5.8 | 0.4 | 90.4 | 0.2 |
| 2 | 3.3 | 5.03 | 0.4 | 90.8 | 0.47 |
| 4 | 3.8 | 4.6 | 0.4 | 90.23 | 0.97 |
| 5 | 4.0 | 4.32 | 0.4 | 90.5 | 0.78 |

The foregoing results show that at high temperature (>220° C.) aniline increases and depletion of both azobenzene and 4-ADPA is observed. At 130° C., however, the increase in aniline is negligible and the 4-ADPA content remains practically unchanged.

Example 4—Concentration of 4-ADPA Mass Below 130° C.

This example illustrates concentration of the 4-ADPA mass at a temperature below 130° C.

Into a 3 liter capacity glass round bottom flask equipped with three feet of distillation column packed with glass packing, a reflux condenser-divider, a receiver flask, 4-ADPA mass (2200 gm) containing aniline (66.4%), azobenzene (2.4%), phenazine (0.28%), 4-ADPA (27.3%) and moisture (3.1%) was charged and then heated to a pot temperature of up to 130° C. under a reduced pressure of about 100 mm Hg and gradually decreased to about 10 mm Hg to distill water & aniline mixture, followed by aniline. The mass obtained after concentration (702 gm) has a composition of aniline (5.8%), 4-ADPA (85.4%), azobenzene (7.7%) and phenazine (0.9%). The analysis indicates that the 4-ADPA and azobenzene contents remained practically remained unchanged.

Example 5—Reduction of Azobenzene in the Organic Mass

This example illustrates a typical reduction of azobenzene in the 4-ADPA mass.

In a 1 liter capacity autoclave, a 4-ADPA concentrated mass (662 gm), containing aniline (5.8%), azobenzene (7.7%), phenazine (0.9%) and 4-ADPA (85.4%) was added along with Ni catalyst and the reaction mixture was heated to 120° C. under a hydrogen pressure of 25 kg/cm$^2$. At the end of the azobenzene reduction (about 0.5 hr), the composition of the 4-ADPA mass shown by GC was aniline (13.6%), azobenzene (<500 ppm), phenazine (0.9%); and 4-ADPA (85.3%).

Example 6—Fractional Distillation Study after Reduction of Azobenzene

This example illustrates that there is much less tar formation and a higher recovery of 4-ADPA using the method of the present invention wherein azobenzene is reduced prior to fractional distillation for recovery of 4-ADPA.

A 4-ADPA reaction mass (605 gm) containing aniline (10.3%), phenazine (0.95%), 4-ADPA (88%), etc. when subjected to fractional distillation under reduced pressure up to 8-10 mm Hg at a pot temperature up to 280° C., showed essentially no increase in the amount of aniline, based on aniline input. Overall, only 1.2% 4-ADPA, based on 4-ADPA input was lost during fractional distillation, as compared to a loss of about 3.2% (depletion in 4ADPA) as shown above in Table 2 of Example D. Also, a smaller amount of distillation residue containing tars and some 4-ADPA was obtained, as compared to fractional distillation of the 4-ADPA containing reaction product as shown in Table 2 of Example D above.

Example 7—Conversion of 4-ADPA to 6PPD

This example illustrates conversion of 4-ADPA (purity >99%) obtained from the process of Example 6 above to N-(1,3-dimethylbutyl)-N'-phenyl-p-phenylenediamine (6PPD), a useful antiozonant for protection of rubber products.

4-ADPA (235.5 gm), methyl isobutyl ketone (MIBK) (177 gm) and 3% Pt/C catalyst (1.2 gm) along with activated charcoal (4.8 grams) was charged into a 1 liter Parr autoclave. After purging with hydrogen the reaction mixture was heated to 155° C. under a hydrogen pressure of 35 kg/cm$^2$. At the end of reduction (about 0.5 hr, typically 4-ADPA 0.25% by GC analysis), the reaction mixture was cooled and filtered to separate it from the catalyst mass. A 6PPD product of 99.2% purity, as measured by GC, was obtained after distillation of water and MIBK.

The same Pt/C catalyst was used for 3 recycles with a maximum alkylation time up to 70 minutes indicating that 4-ADPA obtained from the above process of Example 6 is of good quality since the Pt/C catalyst is not adversely affected by the by-products in the 4-ADPA product during the reduction reaction.

Example E—Impact of Tar Material on Catalyst Activity

This example illustrates the adverse impact of the undesirable tar material that may be carried over during 4-ADPA fractional distillation, on catalyst activity during reductive alkylation of 4ADPA. In this example, 4-ADPA obtained from the process of Example C was converted to N-(1,3-dimethylbutyl)-N'-phenyl-p-phenylene diamine (6PPD).

4-ADPA obtained by the process of Example C (235.5 gm), methyl isobutyl ketone (MIBK) (177 gm) and Pt/C catalyst (1.2 gm) along with activated charcoal (4.8 grams) was charged into a 1 liter Parr autoclave. After purging with hydrogen the reaction mixture was heated to 155° C. under a hydrogen pressure of 35 kg/cm$^2$. At the end of reduction (about 40 min., typically 4-ADPA 0.25% by GC analysis), the reaction mixture was cooled and filtered to separate it from the catalyst mass. The 6PPD product had a 99.2% purity, as measured by GC, was obtained after distillation of water and MIBK.

The catalyst used in this Example, when recycled, resulted in an increase in the alkylation time from 0.5 to 2 hours indicating that the 4-ADPA obtained from the above process of Example C is of inferior quality, since it poisons the catalyst, as shown by the degradation in catalyst activity in subsequent recycle steps.

From the foregoing description, one skilled in the art can easily ascertain the essential characteristics of this invention and without departing from the spirit and scope thereof can make various changes and modifications of the invention to adapt it to various usages and conditions.

The invention claimed is:

1. A process for preparing and isolating 4-aminodiphenylamine comprising the steps of:
   i) reacting aniline and nitrobenzene in the presence of a base catalyst and water under conditions suitable to produce a reaction product comprising one or more salts of 4-nitrosodiphenylamine and 4-nitrodiphenylamine and by-products comprising azobenzene;

ii) adding water and hydrogenating the reaction product from step i) in the presence of suitable hydrogenation catalyst to produce 4-aminodiphenylamine-containing reaction product;

iii) separating the hydrogenation catalyst from the reaction mixture to obtain an aqueous phase comprising base catalyst and organics, and an organic phase comprising 4-aminodiphenylamine, azobenzene and base catalyst; and iv) washing the organic phase with water to reduce base catalyst in the organic phase and/or extracting the aqueous phase with an aromatic hydrocarbon solvent to reduce organics present in said aqueous phase v) extracting the aqueous catalyst recycle phase from step iv) with an aromatic hydrocarbon to remove at least some residual organic phase from the aqueous catalyst recycle phase; and vi) recycling the extracted aqueous catalyst recycle phase from step v) to step i), with optional further purification;

vii) dehydrating the organic phase comprising 4-aminodiphenylamine, azobenzene, and phenazine in excess aniline to remove moisture under a reduced pressure at about 100-110° C.;

viii) fractionally distilling the organic phase comprising 4-aminodiphenylamine, azobenzene, and phenazine at a temperature below 130° C. to obtain a concentrated organic mass with an aniline content of less than 5% w/w;

ix) hydrogenating the concentrated mass from step viii) in the presence of a suitable hydrogenation catalyst to reduce at least some azobenzene to aniline and provide a reduced mass;

x) separating the hydrogenation catalyst from the reduced mass from step ix) by filtration to provide a filtrate, xi) fractionally distilling the filtrate to separate low boiling materials comprising at least aniline and phenazine to provide a distillate and bottoms, xii) recovering 4-aminodiphenylamine having a purity >99% from the bottoms of step xi), xiii) recycling aniline recovered from steps (viii) and (xi) to step (i); and xiv) recycling the hydrogenation catalyst from steps iii) and x) to steps ii) and ix), respectively, and optionally adding fresh hydrogenation catalyst to the recycled hydrogenation catalyst to maintain a required catalyst activity.

2. The process according to claim 1, wherein step (iv) comprises washing organic phase with water to reduce an amount of residual base catalyst in the organic phase.

3. The process according to claim 1, wherein step (iv) comprises extracting the aqueous phase with an aromatic hydrocarbon solvent to reduce an amount of organics present in said aqueous phase.

4. The process according to claim 1, wherein step (iv) comprises washing organic phase with water to reduce an amount of residual base catalyst in the organic phase and/or extracting the aqueous phase with an aromatic hydrocarbon solvent to reduce an amount of organics present in said aqueous phase.

5. The process according to claim 1, wherein the base catalyst is tetramethylammonium hydroxide.

6. The process according to claim 1, wherein in step (i), a molar ratio of water to base catalyst is up to 10:1 at the start of the reaction of aniline with nitrobenzene.

7. The process according to claim 1, wherein in step (i), a molar ratio of aniline to nitrobenzene is from 6:1 to 15:1.

8. The process according to claim 1, wherein in step (i), a molar ratio of aniline to nitrobenzene is from 6:1 to 10:1.

9. The process according to claim 1, wherein in step (i), a molar ratio of base catalyst to nitrobenzene is from 0.8:1 to 1.5:1.

10. The process according to claim 1, wherein a molar ratio of base catalyst to nitrobenzene is from 0.9:1 to 1:1.

11. The process according to claim 1, wherein in step (ii), hydrogenation is performed in the presence of 20 to 50 wt. % of water, relative to total mass upon initiation of hydrogenation.

12. The process according to claim 1, wherein step (iii) is carried out at a temperature of 20-60° C.

13. The process according to claim 2, wherein in step (iv), a weight ratio of water to organic phase is from 0.1:1 to 1:1.

14. The process according to claim 2, wherein in step (iv), a weight ratio of water to organic phase is from 0.2:1 to 0.6:1.

15. The process according to claim 3, wherein in step (iv), a weight ratio of aromatic hydrocarbon solvent to aqueous phase is from 0.1:1 to 1:1.

16. The process according to claim 3, wherein in step (iv), a weight ratio of aromatic hydrocarbon solvent to aqueous phase is from 0.1:1 to 0.4:1.

17. The process according to claim 3, wherein in step (iv), the aromatic hydrocarbon solvent comprises a solvent selected from benzene, toluene, xylene and mixtures thereof.

18. The process according to claim 1, wherein step (iv) is carried out at a temperature of 20-40° C.

19. The process according to claim 1, wherein aqueous phase from step (iv) containing base catalyst is used to form a subsequent reaction mixture for use in step (i).

20. The process according to claim 1, wherein the reaction time for reaction of aniline and nitrobenzene is less than 3.5 hours.

21. The process according to claim 1, wherein the reaction time for reaction of aniline and nitrobenzene is less than 1.5 hours.

22. The process according to claim 1, wherein the nitrobenzene is added to step (i) in one lot.

23. The process according to claim 1, wherein in step (viii) the temperature of the organic phase is maintained during distillation at about 70° C. to about 130° C. and the distillation is carried out at a reduced pressure of about 10 mm Hg to about 100 mm Hg.

24. The process according to claim 1, wherein in step (viii) the temperature of organic phase is maintained during distillation at about 100° to about 130° C. and the distillation is carried out at a reduced pressure of about 10 mm Hg to about 40 mm Hg.

25. The process according to claim 1, wherein in step (viii) the aniline content in the concentrated mass is not more than about 10 wt % at the end of distillation.

26. The process according to claim 1, wherein in step (viii) the aniline content in the concentrated mass is not more than about 6 wt % at the end of distillation.

27. The process according to claim 1, wherein in step (ix) hydrogenation is carried out at a temperature of from about 70° C. to about 140° C. and a pressure of from about 1 kg/cm$^2$ to about 35 kg/cm$^2$ for a hydrogenation time less than about 2 hours whereby at least substantial azobenzene is reduced to aniline.

28. The process according to claim 1, wherein in step (xi) the fractional distillation is carried out at a bottoms temperature of from about 245° C. to about 255° C. and a reduced pressure of about 6 mm Hg to about 12 mm Hg.

29. The process according to claim 28, wherein in step (xii) the recovery of 4-aminodiphenylamine is carried out at a top temperature of from about 190° C. to about 200° C. and a pressure of from about 3 mm Hg to about 5 mm Hg.

30. The process according to claim 1, further comprising the steps of:
(xv) obtaining 4-aminodiphenylamine by purification of the organic phase, and
(xvi) reductively alkylating the 4-aminodiphenylamine from step (xv) to produce at least one alkylated derivative of 4-aminodiphenylamine.

31. The process according to claim 4, further comprising the step of recycling the aqueous phase containing base catalyst to step (i).

32. A process comprising the steps of:
i) reacting aniline and nitrobenzene in the presence of a base catalyst and water under conditions suitable to produce a reaction product comprising one or more salts of 4-nitrosodiphenylamine and 4-nitrodiphenylamine along with one or more by-products comprising at least azobenzene;
ii) adding water and hydrogenating the reaction product from step i) in the presence of suitable hydrogenation catalyst to produce 4-aminodiphenylamine-containing reaction product;
iii) separating the hydrogenation catalyst from the reaction mixture by filtration to obtain an aqueous phase containing at least base catalyst and an amount of organics, and an organic phase containing at least 4-aminodiphenylamine, azobenzene and base catalyst;
iv) dehydrating the organic phase in an excess of aniline to remove moisture under reduced pressure at a temperature of 100-110° C.;
v) fractionally distilling the dehydrated organic phase while maintaining a bottom temperature below 130° C. under reduced pressure for a sufficient time to obtain a product containing at least 4-aminodiphenylamine and azobenzene and having an aniline content of less than 10% w/w;
vi) hydrogenating the product of step v) in the presence of suitable catalyst to reduce azobenzene to a content of less than 500 ppm, thereby increasing an aniline concentration;
vii) separating the product of step vi) from the catalyst; and
viii) fractionally distilling the separated product from step (vii) to recover 4-aminodiphenylamine.

33. The process according to claim 32, further comprising the step of:
ix) recycling aniline recovered from steps (v) and (viii) to step (i).

34. The process according to claim 32, further comprising the step of:
(x) recycling hydrogenation catalyst from steps (iii) and (vii) to step (ii) and step vi), respectively.

35. The process according to claim 34, further comprising the step of adding fresh hydrogenation catalyst to the recycled hydrogenation catalyst in an amount sufficient to maintain a desired catalyst activity.

36. The process according to claim 32, wherein step (viii) is carried out at a bottom temperature of from 245-255° C. and at a reduced pressure of 6-12 mm Hg and step (viii) is carried out at a Top temperature of from 190-200° C. and a pressure of 7 to 4 mm Hg.

37. A process for reacting a reaction mixture comprising aniline and nitrobenzene in the presence of tetramethylammonium hydroxide base under suitable conditions to produce a reaction mass containing tetramethylammonium salts of 4-nitrosodiphenylamine and 4-nitrodiphenylamine, wherein nitrobenzene is added to the reaction mixture in one lot to reduce batch cycle time.

* * * * *